United States Patent [19]

Myers

[11] Patent Number: 4,477,646

[45] Date of Patent: Oct. 16, 1984

[54] PIPERAZINOETHYL UREAS

[75] Inventor: Jimmy Myers, Sweeny, Tex.

[73] Assignee: The Dow Chemical Company, Midland, Mich.

[21] Appl. No.: 525,866

[22] Filed: Aug. 24, 1983

[51] Int. Cl.$^3$ .................... C08G 59/50; C07D 241/04
[52] U.S. Cl. .................................... 528/118; 549/400
[58] Field of Search .................. 521/128; 528/118, 89, 528/93; 544/400

[56] References Cited

U.S. PATENT DOCUMENTS

| | | | |
|---|---|---|---|
| 3,057,809 | 10/1962 | Newey | 521/128 |
| 3,505,335 | 4/1970 | Peerman | 528/118 |
| 3,557,056 | 1/1971 | Peerman | 528/118 |
| 3,957,774 | 5/1976 | Kalopissis et al. | 544/400 |
| 3,977,881 | 8/1976 | Kyburz et al. | 544/400 |
| 4,278,796 | 7/1981 | Corvi-Mora | 544/400 |
| 4,279,804 | 7/1981 | Cantatore et al. | 260/45.8 N |

FOREIGN PATENT DOCUMENTS

| | | | |
|---|---|---|---|
| 0048044 | 3/1982 | European Pat. Off. | 544/400 |
| 3027796 | 2/1982 | Fed. Rep. of Germany | 521/128 |

OTHER PUBLICATIONS

Galstokhova et al., Chemical Abstracts, 74(7), 30660k.
Mukerji et al., Chemical Abstracts, 90(5), 338620.
Wang et al., Chemical Abstracts, 90(23), 186903l.

Primary Examiner—John Kight, III
Assistant Examiner—Kriellion Morgan
Attorney, Agent, or Firm—J. G. Carter

[57] ABSTRACT

Novel piperazinoethyl ureas are prepared by reacting an aminoethyl piperazine with urea and recovering the monosubstituted urea product. These products are useful as curing agents for epoxy resins.

17 Claims, No Drawings

PIPERAZINOETHYL UREAS

BACKGROUND OF THE INVENTION

The present invention pertains to novel piperazinoethyl urea compounds and method for their preparation.

Urea compounds are well known in the art. However, a novel class of monosubstituted urea compounds have been discovered which constitute the present invention.

SUMMARY OF THE INVENTION

The present invention is directed to a compound or mixture of compounds represented by the formula

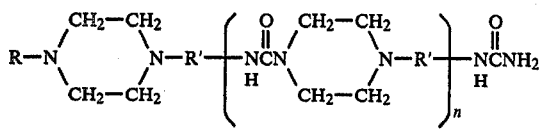

wherein R is hydrogen or a hydrocarbyl group having from 1 to about 12, preferably from about 1 to about 5, carbon atoms, R' is a divalent hydrocarbyl group having from 1 to about 12, preferably from about 2 to about 5, carbon atoms and n has an average value from zero to about 30, preferably from zero to about 15, most preferably from zero to about 8.

Another aspect of the present invention pertains to a curable adduct formed by reacting a composition comprising (A) the aforementioned compounds where n is zero and (B) an epoxy resin in a molar ratio of (A):(B) of from about 0.7:1 to about 3.4:1; preferably from about 1:1 to about 2:1.

Still another aspect is a cured product resulting from reacting a composition comprising (1) the aforementioned curable adduct and (2) an epoxy resin in a molar ratio of (1):(2) of from about 0.5:1 to about 2.5:1, preferably from about 0.7:1 to about 1.4:1.

DETAILED DESCRIPTION OF THE INVENTION

The novel compounds of the present invention are prepared by reacting urea with aminoethylpiperazine, a substituted aminoethyl piperazine or mixtures thereof at temperatures of from about 80° C. to about 135° C., preferably from about 90° C. to about 100° C. Hereafter, said aminoethylpiperazine and hydrocarbon substituted aminoethylpiperazine are referred to collectively as piperazine compound.

Any pressure from subatmospheric to superatmospheric can be employed with atmospheric pressure being preferred.

If desired, the reaction between the piperazine compound and urea can be conducted in the presence of a polar solvent such as, for example, water, ketones, alcohols, glycols, mixtures thereof and the like.

Suitable piperazine compounds which can be employed herein include, for example, N-aminoethylpiperazine, N-aminopropylpiperazine, mixtures thereof and the like.

The product can be separated from the reaction mass by any desired means such as, for example, crystallization, filtration, decanting of liquid phase or stirring crystalline product into acetone and filtering off solids. For the latter, the acetone can be removed using a rotary evaporator and vacuum pump or a vacuum oven, combinations thereof and the like.

Any reaction medium can be removed by distillation and the like.

If desired, catalysts such as, for example, basic ion exchange resins, quaternary ammonium compounds, phosphonium compounds, mixtures thereof and the like can be employed in preparing the compounds of the present invention.

Suitable basic ion exchange resins include, for example Dowex MSA-1 (chloride or hydroxide form), Dowex I, 2, 21K, or 11.

Suitable quaternary ammonium compounds include, for example, benzyltrimethylammonium chloride, benzyltrimethylammonium bromide, benzyltrimethylammonium hydroxide, tetramethylammonium chloride, tetramethylammonium bromide, tetramethylammonium hydroxide.

Suitable phosphonium compounds include, for example, tetra(hydroxymethyl)phosphonium chloride, tetra(hydroxymethyl)phosphonium bromide, tetra(hydroxymethyl)phosphonium iodide, ethyltriphenylphosphonium chloride, ethyltriphenylphosphonium bromide, ethyltriphenylphosphonium iodide, butyltriphenylphosphonium chloride, butyltriphenylphosphonium bromide, butyltriphenylphosphonium iodide, methyltriphenylphosphonium chloride, methyltriphenylphosphonium bromide, methyltriphenylphosphonium iodide, tetrabutylphosphonium chloride, tetrabutylphosphonium bromide, tetrabutylphosphonium iodide, methyltributylphosphonium chloride, methyltributylphosphonium bromide, methyltributylphosphonium iodide, mixtures thereof and the like.

The compounds of the present invention are useful as curing agents and/or accelerators for epoxy resins.

The following examples are illustrative of the invention but are not to be construed as to limiting the scope thereof in any manner.

EXAMPLE 1

To a 1-liter reaction flask equipped with a mechanical stirrer, thermometer, $I^2R$ temperature controller, and water cooled condenser was added 4.86 moles (4.86 equivalents of primary amine) or 628 grams of N-(2-aminoethyl)piperazine (AEP). Then 0.93 gram (0.12 wt. % of total) of 2-methyl imidazole was added as a catalyst. The reaction solution was then heated to 120° C. while stirring well and controlled at this temperature. Then 2.5 moles (5 equivalents) of urea was added manually in 4 increments over a 2.13 hours (7668 s) period. The reaction was allowed to digest at 120° C. for an additional 3.5 hours (12,600 s). Two small samples were taken during this time and titrated with 1 N HCl using bromthymol blue as the indicator to determine the % conversion. The formula used to determine % conversion was:

$$\frac{(\text{initial Amine Equiv.} - \text{Final Amine Equiv.}) (100)}{\text{Initial Amine Equivalents}} =$$

% conversion of original hydrogen bonded nitrogen equivs.

The second sample taken gave 7.03 equivalents of amine remaining. The % conversion using the formula was calculated as:

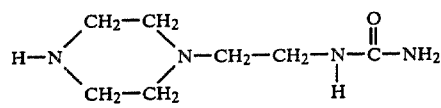
= 27.67% conversion of the original hydrogen bonded nitrogen equivs.

The heat and stirrer was turned off and reaction solution allowed to cool to ambient temperature (~25° C.). About 80 volume % of the reaction flask crystallized. A sample of this crude product (crystals and liquid) was found to contain 48 area % 1-(2-piperazinoethyl)urea, 33 area % unreacted aminoethylpiperazine, and about 19 area % unknown impurities. The crude crystalline product (722 grams) was placed in a large vessel containing 1444 grams of acetone and stirred mechanically for 15 minutes (900 s). The crystalline product was then separated from the liquid phase by filtering through a medium sintered glass funnel using a vacuum flask. A second extraction was made using fresh acetone and filtered as before. The residual acetone was removed using a rotary evaporator at 30° to 40° C. and less than 1 mm Hg absolute pressure. A white crystalline solid was obtained having a melting point of 147° C. to 152° C. The amine nitrogen equivalent weight calculated by titrating with 1 N HCl was 168.14 compared to 172.27 (theory). This product was greater than 90% pure as confirmed by liquid chromatography. Analysis by NMR and infrared were used to identify the product as 1-(2-piperazinoethyl) urea which can be represented by the following general formula $$\begin{array}{c} \phantom{H-N}CH_2-CH_2 \\ H-N\phantom{-}\phantom{CH_2-CH_2}N-CH_2-CH_2-N-C-NH_2 \\ \phantom{H-N}CH_2-CH_2\phantom{N-CH_2-CH_2-}\underset{H}{|}\phantom{-C-}\overset{O}{\|} \end{array}$$

EXAMPLE 2

To a 1-liter flask (baffled to increase turbulence during mixing) and equipped with a condenser, mechanical stirrer, thermometer, heat lamp and temperature controller was added 3.92 moles or 7.84 urea amide equivalents (235.44 grams) of urea. While at ambient temperature (~25° C.) 3.92 moles or 7.84 amine equivalents (516.84 grams) of aminoethylpiperazine was added. The mixture was stirred to keep the solid urea suspended while heating to 100° C. About 80 to 90% of the urea had dissolved at 70° C. but some solid urea was noted until about 92° C. was obtained. A temperature of 100° C. was reached after about 1.5 hours (5400 s). After about 15 minutes (900 s) at 100° C. ammonia was being given off through the condenser at a rate easily detectable by holding a stopper from an HCl bottle above the condenser. The reaction temperature was maintained at 100° C. and samples were titrated periodically with 1 N HCl to determine % conversion using the formula as given in example 1. At 24 hours (86400 s) after initial heating the reaction solution suddenly crystallized into a solid which prevented further mixing. The heat lamp was immediately turned off. It was found by titrating a sample with 1 N HCl that a conversion of 46.2% of the original amine equivalents was obtained. A total net weight of 682.7 grams crystalline material was obtained. After adding about 3 grams as a loss from sampling, the yield based on NH$_3$ loss for a 46.2% conv. was calculated as 99.3%. The product weight percent composition as analyzed by liquid chromatography was 86.55% 1-(2-piperazinoethyl)urea, 0% urea, 2.68% AEP and 10.77% by-product. The amine equivalent weight (based on titration) was 161.47 compared to 172.27, theory.

EXAMPLE 3

To a 1-liter baffled flask equipped with a mechanical stirrer, condenser, heat lamp, thermometer and temperature controller was added 4 moles or 8.0 equivalents of aminoethylpiperazine. After heating to about 120° C., 240.4 grams, 4 moles or 8.0 equivalents of urea was added manually over a 4 minute (240 s) period. The reaction temperature was maintained at 120° C. Samples were titrated periodically for % conversion in the same manner as described in Example 1. After 3.95 hours (14220 s) from initially adding the urea, a conversion of 49.6% of the original hydrogen bonded nitrogen was obtained as determined by titrating with 1 N HCl. The reaction mixture, still a low viscosity material at this temperature, was cooled down and reweighed. A light yellow resinous material was obtained which was highly viscous at ambient temperature (~25° C.). After a few days the total contents of the bottled material had crystallized. The yield was calculated as 98.9% and had an amine equivalent weight of 171.32 which compares to theory of 172.27. The weight % composition as analyzed by liquid chormatography was 95.09% 1-(2-piperazinoethyl)urea, 0.45% urea, 2.56% AEP and 1.90% unknown by-products.

EXAMPLE 4

To a 4-liter resin kettle equipped with a mechanical stirrer, condenser, heat lamps and temperature controller was added 17.838 moles (35.676 equivalents) of aminoethylpiperazine. At ambient temperature (~25° C.) 17.838 moles (35.676 equivalents) of urea was added. The solid urea and AEP was mechanically stirred and heated to ~100° C. over ~1.87 hours (6720 s). All urea had dissolved at 97° C. The reaction was controlled at ~100° C. for 17.85 hours (64,260 s). At this point a sample titrated and calculated by the method given in Example 1 gave 39.91% conversion of original amine equivalents. The reaction solution was then heated to 120° C. over a 0.87 hour (3120 s) period and controlled at this temperature for 3.67 hours (13,200 s). A total net weight of 3139.5 grams (~100% yield) of crude product, light yellow in color was obtained which upon cooling to ambient temperature (~25° C.) became a very viscous liquid or semisolid. After 1 day (86400 s) a slight warming was used in order to transfer liquid product and upon cooling to ambient temperature (~25° C.) crystallization occured to give white pasty solids. A sample titrated in the same manner as in Example 1 gave 48.60% conversion and an amine equivalent weight of 171.55 which compares to 172.27 for theory. The weight percent composition as analyzed by liquid chromatography was 79.13% 1-(2-piperazinoethyl)urea, 0% urea, 1.29% AEP and 19.58% other components mostly high molecular weight polymer.

EXAMPLE 5

To a 1-liter flask (baffled to increase turbulence during mixing) and equipped with a condenser, mechanical stirrer, thermometer, heat lamp and temperature controller was added 516.84 grams (4 moles or 8 amine equivalents) of N-(2-aminoethyl)piperazine. Stirring was begun and the flask was heated up to 120° C. and controlled at this temperature. A total of 240.24 grams (4 moles or 8 urea amide equivalents) were added manually in 3 portions over a 2.23 hours (8040 s) period. Stirring and heating was continued for 2.78 hours (10,020 s). Samples were analyzed by liquid chromatography throughout the reaction and this run was stopped just when the urea remaining had been reduced to nil. This prevents over-reaction where the amine equivalent weight increases dramatically. Upon titrating the final product by the method given in Example 1 the conversion of original amine was 51.75%. A light yellow liquid product was obtained which crystallized upon cooling to paste-like white solids. The net weight of bottled product plus samples taken was 682.9 grams which calculates as 99.45% yield. The weight % composition as analyzed by liquid chromatography was 85.97% 1-(2-piperazinoethyl)urea, 1.60% urea, 1.55% AEP and 10.88% by-products. An amine equivalent weight of 176.76 was determined by titrating with 1 N HCl. This compares to 172.27 theory.

EXAMPLE 6

To a 1-liter resin kettle equipped with a condenser, mechanical stirrer, thermometer, heat lamp and temperature controller was added 680.94 grams (5.27 moles) of N-(2-aminoethyl)piperazine. The stirrer and heat lamp was turned on. After a temperature of 90° C. was reached a total of 316.52 grams (5.27 moles) of urea was added over a 3 minute (180 s) period of time. During this time the reaction temperature dropped to 70° C. because of the addition. The temperature was increased to 100° C. and controlled for about 6 hours (21,600 s). Then the reaction temperature was increased to 113° C. for about 17 hours (61,200 s) and then controlled at 110° C. for 2 hours. The total reaction time was 25.08 hours (90,300 s).

An amber colored liquid resin was obtained which had an amine equivalent weight of 205.74 as calculated by titrating a sample with 1 N HCl using bromthymol blue indicator. Then the formula used was sample weight (grams)/amine equivalent titrated=amine equivalent weight.

This material was analyzed by infrared analysis, nuclear magnetic resonance (NMR) analysis and gel permeation chromatography. The weight percent composition was found to be about 47.50% mono AEP/urea adduct, 10.90% n=1 AEP/urea polymer, 36.80% n=2 AEP/urea polymer. The total net weight was 860.5 grams which was equal to a 96.8% yield based on theoretical ammonia loss.

EXAMPLE 7

A net weight of 108 grams of amber colored resin from Example 6 was added to a 250 ml reaction flask equipped with a mechanical stirrer, thermometer, heat lamp, temperature controller and water cooled condenser. The stirrer and heat lamp were turned on and the temperature was increased to 110° C. in 5 minutes (300 s). Then the reaction temperature was maintained in a 110° C. to 147° C. range for a total heating time of 24.17 hours (87,012 s). A sample was then taken and found to have an amine equivalent weight of 452.32 by titrating with 1 N HCl and using the formula given in Example 6.

The stirring was continued while maintaining a reaction temperature of about 119° C. for an additional 52.95 hours (194,397 s). The heat lamp was turned off and allowed to cool to ambient temperature. A very viscous liquid at ambient temperature was obtained. It was found that the viscosity was greatly reduced by warming slightly to about 40° C. to 60° C. with a heat lamp. A sample was mixed with water and found to be completely miscible in all proportions.

The amine equivalent weight was determined to be 464.41 by titrating with 1 N HCl which is equivalent to an "n" value of 1.86 in the following structure.

The theoretical amine equivalent weight for

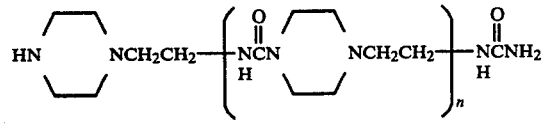

where n=2 was 482.27.

A confirmation of the "mono" and "multi" substituted urea groups were obtained by NMR analysis and further supported by infrared analysis.

The product was analyzed by liquid chromatography and found to contain components varying from about n=0 to about n=10. The average amine equivalent weight as calculated by liquid chromatography was 514.02 which was equivalent to an average "n" repeating units of 2.20.

EXAMPLE 8

Curing of Product from Example 7 with Epoxy Resin

Into a 2 oz. bottle was placed 0.66 grams of product from Example 7 (464.47 amine equivalent weight). Then 0.94 grams DER ® 383, a diglycidyl ether of bisphenol A epoxy resin (Epoxide Equivalent Weight=188). The two components were hand stirred while heating with a close heat lamp. After a temperature of 140° C. was reached due to external heating with no apparent thickening or curing then 0.04 grams of 2-methylimidazole solids were added and stirred into the mix. After about 2 minutes (120 s) the mixture began to thicken exotherm and cure to a solid material. The color changed from a straw yellow to a deep red color. The cured polymer was very tough and could not easily be broken by hand.

EXAMPLE 9

Curing of Diglycidyl Ether of Bisphenol A with Mono AEP/Urea Adduct as Hardener

To a 2 oz. glass bottle was added 5.38 grams of crude mono AEP/urea adduct from Example 2 (amine equivalent weight of 161.47 by HCl titration) and 18.80 grams of DER ® 383, a diglycidyl ether of bisphenol A (epoxide equivalent weight of 188). A heat lamp was adjusted to the side of bottle to heat up the mixture, while hand stirring to disperse the solid mono AEP/urea adduct. At about 74° C. the solids began dissolving and in less than 1 minute (60 s) an exotherm had begun. At 95° C. all the solids had dissolved giving a nonturbid straw-yellow color to the mix. A portion of the mix was quickly poured into a test tube (15 cm length and 1.8 cm inside diamter) premarked to show division in centimeters (cm). The test tube was filled to the 4 cm mark. Within a few seconds the mix thickened and foaming began. The quick curing entrapped the bubbles in the foam and prevented the bubbles from breaking the surface of the curing mix and in effect caused the volume to expand. The total volume expansion was from 4.0 cm to 6.3 or 158% expansion.

EXAMPLE 10

Curing of Diglycidyl Ether of Bisphenol A with Mono AEP/Urea Adduct via Prepolymer Formation To a 2 oz. bottle No. 1 (8 cm length, 3.7 cm inside diameter) was added 8.08 grams of crude mono AEP/urea adduct (161.47 amine equivalent weight) from Example 2 and 9.40 grams DER ® 383 (188 Epoxide Equivalent Weight). In a 2nd bottle was placed 17.48 grams DER ® 383 and a heat lamp was adjusted to keep the temperature at about 70° C.

Now a heat lamp was directed onto the side of bottle No. 1 and the mix was hand stirred to disperse and dissolve and/or react the solid mono AEP/urea adduct. After about 15 minutes (900 s) of stirring at about 70° C. the solids became well dispersed. Then an additional 8.70 grams of DER ® 383 from the second bottle was added to bottle No. 1 to dissolve and/or react the solid phase. At about 80° C. all the solids had dissolved giving a clear one-phase mixture.

Quickly the remainder of the DER ® 383 (8.78 grams) was added and the epoxy resin stirred in by hand using a metal spatula wherein the mix soon* thickened and began to foam.

*Note: There was only about 1.5 minutes (90 s) between the mix being a clear low viscosity liquid (at 85° C.) and the thickening phase.

The foaming continued over about 30 seconds and an exotherm (>150° C.) was noted. The entrapped bubbles from the foaming caused the polymer to protrude above the bottle by about 3 cm. The total expansion was from 3.2 cm initially to 11.2 cm after curing or 350%. Upon cooling the polymer was non-tacky and rigid.

EXAMPLE 11

Cure of Epoxy Resin Using Mono AEP/Urea-AEP Blend to Give Epoxy Foam

Into a 2 oz. bottle was added 1.7 grams (0.11 amine hydrogen equivalents) of solid mono AEP/urea from Example 2 (161.47 amine equivalent weight) and 3.6 grams (0.084 amine hydrogen equivalents) of aminoethylpiperazine. The bottle was heated to 70° C. to 80° C. using a heat lamp while hand stirring to dissolve all the mono AEP/urea solids. Into a 2nd bottle was added 17.3 grams (0.095 epoxide equivalents) of DER ® 383 (diglycidyl ether of bisphenol A with an epoxide equivalent weight of 188) and a heat lamp was adjusted to maintain a temperature of about 40° C.

Now the 17.3 grams of DER ® 383 from the 2nd bottle was added to the 1st bottle and stirred while continually heating with a heat lamp. After about 6 minutes (360 s) of heating in which the temperature rose from 60° C. to 70° C. the mix began to foam and thicken. The appearance changed from a clear light yellow liquid to a light yellow solid foam with numerous fine sized entrapped bubbles. The exotherm was recorded as being >150° C. limit of thermometer used. The rapid foaming while curing caused a volume expansion of about 275%. After cooling to ambient temperature the material remained a tough rigid polymer. Pieces were broke off and placed in small vials containing acetone and also water. After 4 days no significant swelling or degradation of the cured foam could be noticed.

I claim:

1. A compound or mixture of compounds represented by the general formula

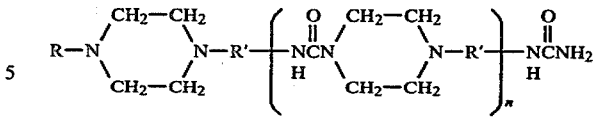

wherein R is hydrogen or a hydrocarbyl group having from 1 to about 12 carbon atoms, R' is a divalent hydrocarbyl group having from 1 to about 12 carbon atoms and n has an average value of from zero to about 30.

2. A compound of claim 1 wherein R is hydrogen and R' is —$CH_2$—$CH_2$— and n has an average value of from zero to about 15.

3. A compound of claim 2 wherein n has an average value of from about zero to about 8.

4. A process for preparing a compound or mixture of compounds of claims 1, 2 or 3 wherein an excess above stoichiometric quantity of N-aminoethylpiperazine, N-substituted hydrocarbyl derivative these of or mixture thereof is reacted with urea and the reaction is conducted at a temperature of from 60° C. to about 135° C.

5. A process for preparing a compound or mixture of compounds of claims 1, 2 or 3 wherein an essentially stoichiometric quantity of N-aminoethylpiperazine, N-substituted hydrocarbyl derivative thereof or mixture thereof is reacted with urea and the reaction is conducted at a temperature of from about 90° C. to about 100° C. and the reaction is conducted in the absence of a solvent.

6. A product resulting from curing an epoxy resin with a curing amount of a compound or mixture of compounds of claims 1, 2 or 3.

7. A product of claim 6 wherein said epoxy resin is a polyglycidyl ether of a polyhydric aromatic compound.

8. A product of claim 7 wherein said epoxy resin is a diglycidyl ether of bisphenol A.

9. A curable adduct formed by reacting a composition comprising (A) a compound or mixture of compounds of claims 1, 2 or 3 wherein n has a value of zero and (B) an epoxy resin in a molar ratio of A:B of from about 0.7:1 to about 3.4:1.

10. An adduct of claim 9 wherein the molar ratio is from about 1:1 to about 2:1.

11. An adduct of claim 10 wherein R is hydrogen and said epoxy resin is a diglycidyl ether of bisphenol A.

12. A cured product resulting from reacting a composition comprising (1) an adduct of claim 9 with (2) an epoxy resin in a molar ratio of (1):(2) of from about 0.5:1 to about 2.5:1.

13. A cured product resulting from reacting a composition comprising (1) an adduct of claim 8 with (2) an epoxy resin in a molar ratio of (1):(2) of from about 0.5:1 to about 2.5:1.

14. A cured product resulting from reacting a composition comprising (1) an adduct of claim 11 with (2) an epoxy resin in a molar ratio of (1):(2) of from about 0.5:1 to about 2.5:1.

15. A cured product of claim 12 wherein the ratio of (1):(2) is from about 0.7:1 to about 1.4:1.

16. A cured product of claim 13 wherein the ratio of (1):(2) is from about 0.7:1 to about 1.4:1.

17. A cured product of claim 14 wherein the ratio of (1):(2) is from about 0.7:1 to about 1.4:1.

* * * * *